United States Patent
Huynh et al.

(10) Patent No.: US 8,332,039 B1
(45) Date of Patent: Dec. 11, 2012

(54) METHOD OF ELECTRICALLY STIMULATING TISSUE OF A PATIENT BY CALIBRATING STIMULATION AMPLITUDE

(75) Inventors: Jeffrey C. Huynh, Dallas, TX (US); Patrick M. Cullen, Dallas, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 585 days.

(21) Appl. No.: 12/511,792

(22) Filed: Jul. 29, 2009

Related U.S. Application Data (60) Provisional application No. 61/084,495, filed on Jul. 29, 2008.

(51) Int. Cl.
*A61N 1/00* (2006.01)
(52) U.S. Cl. .............................................. 607/59; 607/2
(58) Field of Classification Search ................. 607/2, 59
See application file for complete search history.

(56) References Cited

U.S. PATENT DOCUMENTS

| | | | |
|---|---|---|---|
| 6,393,325 B1 | 5/2002 | Mann et al. | |
| 7,254,446 B1 | 8/2007 | Erickson et al. | |
| 7,295,876 B1 | 11/2007 | Erickson | |
| 7,738,963 B2 | 6/2010 | Hickman et al. | |
| 7,747,330 B2 | 6/2010 | Nolan et al. | |
| 2004/0116978 A1 | 6/2004 | Bradley | |
| 2006/0229688 A1 | 10/2006 | McClure et al. | |
| 2007/0203543 A1* | 8/2007 | Stone et al. | 607/59 |

FOREIGN PATENT DOCUMENTS

WO   0193953 A1   12/2001

* cited by examiner

*Primary Examiner* — Niketa Patel
*Assistant Examiner* — Nicole F Lavert
(74) *Attorney, Agent, or Firm* — Christopher S. L. Crawford; Craig Hoersten (57) ABSTRACT

A method comprises: selecting a plurality of electrodes of one or more stimulation leads, the selected plurality of electrodes defining a two-dimensional region; determining a calibration value for stimulation points defined by the plurality of electrodes; selecting a stimulation point within a boundary formed by the two-dimensional region; identifying points on the boundary that are axially displaced relative to the selected stimulation point; automatically calculating boundary calibration values for identified points, each boundary calibration value being calculated as a linear interpolation of calibration values of a pair of stimulation points determined for the plurality of electrodes; automatically assigning a calibration value to the selected stimulation point that is a summation of the calculated boundary calibration values; and using the automatically assigned calibration value for the stimulation point to control an amplitude of stimulation pulses applied to the patient.

10 Claims, 5 Drawing Sheets

METHOD OF ELECTRICALLY STIMULATING TISSUE OF A PATIENT BY CALIBRATING STIMULATION AMPLITUDE

CROSS-REFERENCE TO RELATED APPLICATIONS

This application claims the benefit of U.S. Provisional Application No. 61/084,495, filed Jul. 29, 2008, the disclosure of which is incorporated herein by reference.

TECHNICAL FIELD

The present application is generally directed to programming an implantable pulse generator to provide an electrical stimulation therapy that is calibrated according to measured perception threshold and maximum tolerable values at selected points.

BACKGROUND

Neurostimulation systems are devices that generate electrical pulses and deliver the pulses to nerve tissue to treat a variety of disorders. Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generation circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Spinal cord stimulation (SCS) is an example of neurostimulation in which electrical pulses are delivered to nerve tissue in the spine typically for the purpose of chronic pain control. Other examples include deep brain stimulation, cortical stimulation, cochlear nerve stimulation, peripheral nerve stimulation, vagal nerve stimulation, sacral nerve stimulation, etc. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Also, each exterior region, or each dermatome, of the human body is associated with a particular spinal nerve root at a particular longitudinal spinal position. The head and neck regions are associated with C2-C8, the back regions extends from C2-S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6-L1, lower extremities are located from L2 to S2, and the perineum from L4 to S4. In conventional neurostimulation, when a patient experiences pain in one of these regions, a neurostimulation lead is implanted adjacent to the spinal cord at the corresponding spinal position. By example, to address chronic pain sensations that commonly focus on the lower back and lower extremities using conventional techniques, a specific energy field is typically applied to a region between vertebrae levels T8 and T12.

Stimulation of neural tissue of the spinal cord does not necessarily produce a uniform response up and down the spinal cord. For example, a stimulation pulse of a given amount of current may produce a moderate perception of paresthesia at one vertebral level and may produce a painful sensation at another vertebral level. Accordingly, when creating a stimulation therapy for a patient, it is desirable to prevent such over-stimulation when shifting between electrodes on a stimulation lead. Certain calibration methodologies are known to address this issue. Calibration typically involves determining certain calibration values (e.g., perception threshold and maximum tolerable) that define an allowable range of stimulation amplitudes. To make calibration more efficient, U.S. Pat. No. 7,254,446 describes a methodology where amplitude ramping for patient feedback to determine new calibration values occurs more quickly by using one or more previously determined calibration values.

SUMMARY

In one embodiment, a method uses one or more calibration values for one or more stimulation leads implanted within the epidural space of a patient to control electrical stimulation of the patient. The method comprises: selecting a plurality of electrodes of the one or more stimulation leads, the selected plurality of electrodes defining a two-dimensional region of stimulation points; determining a calibration value for stimulation points defined by the plurality of electrodes; selecting a stimulation point within a boundary formed by the two-dimensional region; identifying points on the boundary that are axially displaced relative to the selected stimulation point; automatically calculating boundary calibration values for identified points, each boundary calibration value being calculated as a linear interpolation of calibration values of a pair of stimulation points determined for the plurality of electrodes; automatically assigning a calibration value to the selected stimulation point that is a summation of the calculated boundary calibration values; and using the automatically assigned calibration value for the stimulation point to control an amplitude of stimulation pulses applied to the patient.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is

DETAILED DESCRIPTION

Figure 1:
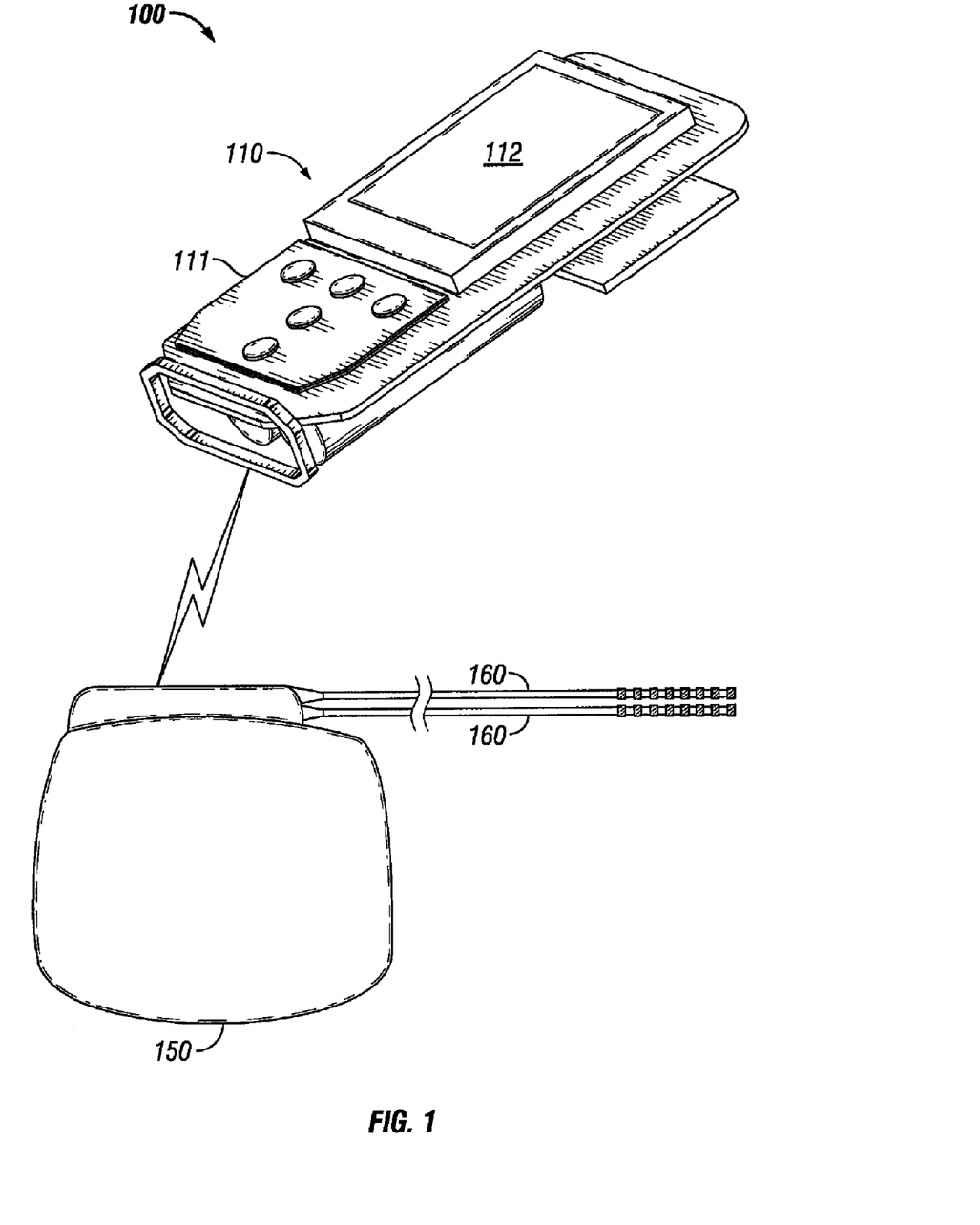
FIG. 1 depicts a medical device system including a controller for controlling an implantable pulse generator according to one representative embodiment.

FIG. 1 depicts medical device system 100 including controller 110 for controlling implantable pulse generator 150 according to one representative embodiment. Pulse generator 150 may be adapted to generate electrical pulses to treat any number of neurological diseases or conditions. Pulse generator 150 can be implanted at any suitable location within a patient such as the lower abdominal region, lower back region, subclavicular region, etc.

Implantable pulse generator 150 typically comprises a metallic housing that encloses pulse generating circuitry, control circuitry, communication circuitry, battery, etc. of the device. An example of pulse generating circuitry is described in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. A microprocessor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference. An example of a commercially available implantable pulse generator is the EON® pulse generator available from St. Jude Medical Neuromodulation Division. Although an implantable pulse generator is described according to some embodiments, other pulse generators could be similarly programmed. For example, an external trial stimulator may be programmed according to alternative embodiments.

One or more stimulation leads 160 are electrically coupled to the pulse generating circuitry of pulse generator 150, e.g., through the electrical contacts of the header of pulse generator 150 or through a lead extension device. As shown in FIG. 1, the two stimulation leads 160 are percutaneous stimulation leads, although any suitable type of stimulation lead can be employed. Examples of commercially-available stimulation leads are the Octrode® percutaneous lead and the LAMITRODE TRIPOLE 8™ paddle lead available from St. Jude Medical Neuromodulation Division of Plano, Tex. Electrical pulses from pulse generator 150 are conducted through the conductors of lead body of stimulation lead(s) 160 and to the electrodes of lead(s) 160.

As shown in FIG. 1, controller 110 comprises input controls 111 for receiving input from the user and display 112 for displaying information to the user. In some embodiments, display 112 may alternatively or additionally implement "touch-screen" functionality to permit the user to provide input by contacting various locations of display 112. Controller 110 further comprises a processor (not shown) for controlling the operations of controller 110 and memory (not shown) for storing data and software code. The memory need not be a single storage medium or device. As used herein, memory collectively refers to the various memory storage components of controller 110 (such as RAM, ROM, magnetic-media storage devices, solid-state storage, etc.). Also, controller 110 is depicted as a single device. In alternative embodiments, controller 110 could be implemented using software stored on a computer that is communicatively coupled to another device that conducts communications directly with pulse generator 150. The software stored in controller 110 enables the user to control implantable pulse generator 150 via display 112 and controls 111. Specifically, controller 110 may be employed by a clinician to program pulse generator 150.

When used to initially program implantable pulse generator 150 or to subsequently revise such programming, the clinician selects values for a number of programmable parameters in order to define the stimulation therapy to be delivered to a patient. The clinician may select pulse amplitude, pulse width, pulse frequency, and electrode combinations. The clinician may also combine multiple sets of such stimulation parameters to define one or more "multi-stimulation set" programs, which are known in the art. The multi-stimulation set programs may allow pain in distinct regions of the body to be treated simultaneously, to permit differences in therapy to be delivered at different times of the day or for different patient activities, etc.

Controller 110 preferably stores software code defining a number of interfaces to facilitate the selection of stimulation parameters and stimulation programs. The screens of the various interfaces are provided to the clinician via display 112 and the clinician inputs data relevant for the various screens using controls 111 and/or the touch-screen functionality of display 112. Upon selection of the respective stimulation parameters, controller 110 communicates the stimulation parameters to pulse generator 150 (preferably using a suitable wireless RF signal) using suitable communication circuitry as is known in the art.

In preferred embodiments, controller 110 stores software code that permits a clinician to calibrate a number of electrode combinations in an efficient manner. The software enables a clinician to define perception threshold and maximum tolerable values for a limited number of electrode combinations by ramping pulse amplitudes and receiving feedback from the patient in a conventional manner. Upon a determination of such values by the clinician, the software automatically calculates respective perception threshold and maximum tolerable values for other electrode combinations.

Figure 2:
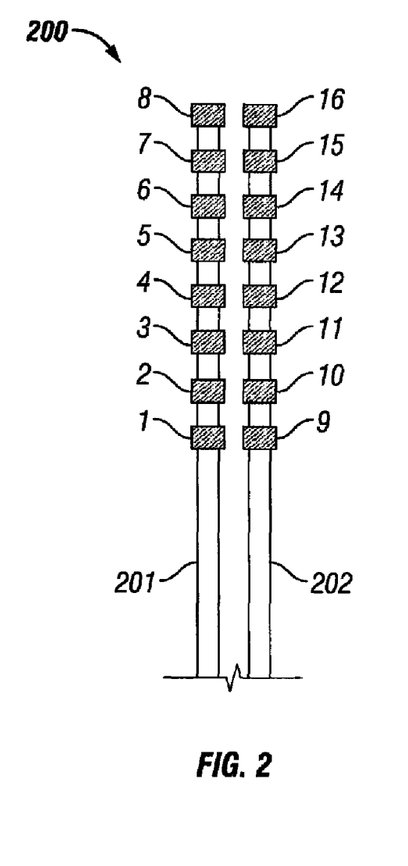
FIG. 2 depicts a lead arrangement that comprises two percutaneous leads arranged in a largely co-aligned manner.

FIG. 2 depicts lead arrangement 200 that comprises two percutaneous leads 201, 202 arranged in a largely co-aligned manner. Lead 201 comprises electrodes 1-8 and lead 202 comprises electrodes 9-16. An example of a commercially available percutaneous stimulation lead comprising such an arrangement of electrodes is the OCTRODE® percutaneous lead from St. Jude Medical Neuromodulation.

Figure 3:
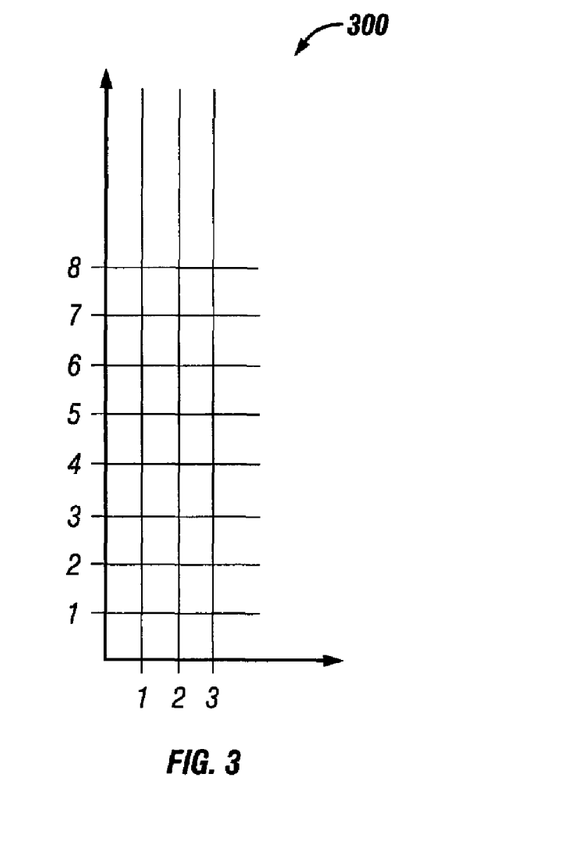
FIG. 3 depicts a grid of stimulation points that corresponds to the electrodes disposed according to the lead arrangement FIG. 2.

FIG. 3 depicts grid 300 of stimulation points that corresponds to the electrodes of arrangement 200 of FIG. 2. A similar grid can be defined for any suitable arrangement of electrodes in relation to the anode/cathode combinations available for a particular arrangement of electrodes. Preferably, distinct calibration values are assigned for each stimulation point within grid 300. Thus, when stimulation is moved from one point to another point within grid 300, the applied amplitude is modified in relation to the calibration values associated with the various points.

Calibration typically involves determining a perception threshold value and a maximum tolerable value. The perception threshold value is a value that represents the minimum required amplitude for a patient to perceive stimulation at the respective stimulation point. The maximum tolerable value represents the maximum amplitude that is tolerable for the patient at the respective stimulation point. These two values are typically utilized to define a range of possible amplitude values at the respective stimulation point. In some embodiments, when moving stimulation between a first stimulation point and a second stimulation point (e.g., during programming), (i) the amplitude used for stimulation at the first point is retrieved; (ii) the following value is calculated: (the retrieved amplitude minus the perception threshold value of the first point) divided by (the maximum tolerable value of the first point minus the perception threshold value of the first point); (iii) the difference between the maximum tolerable value of the second point and the perception threshold value of the second point is calculated; and (iv) the amplitude for stimulation at the second point is set to equal the perception threshold value of the second point plus the calculated value from (ii) times the calculated difference from (iii). Alternatively, an nominal amplitude value can be defined in relative terms for scaling within the range defined between a perception threshold and a maximum tolerable value. For example, a nominal amplitude value between 0-100 (or any other suitable range) can be provided for selection by the clinician. The actual amplitude applied at any particular electrode combination would then fall within the amplitude range defined by the threshold value and the maximum tolerable value in relation to the selected nominal amplitude value. For example, an amplitude step value may be calculated to equal (the maximum tolerable value minus the threshold value) divided by 100. The actual amplitude would then equal the nominal amplitude value times the amplitude step value plus the threshold value.

Using amplitude ranges defined in this manner causes the stimulation perceived by the patient to occur in a largely consistent manner across the electrode positions defined by the electrodes of the lead(s). Specifically, by moving or shifting the electrode combinations, the applied amplitude will be perceived by the patient to be relatively the same. That is, the patient should not typically experience a significant change in the perceived strength of stimulation when the active electrodes are shifted or moved and the nominal amplitude is held constant. Also, painful or otherwise undesirable overstimulation can be avoided.

Determining the calibration values for each stimulation position in grid 300 in response to patient feedback can be a time consuming activity. Slowly ramping the amplitude of pulses applied to a patient to determine a perception threshold and a maximum tolerable limit for each position in grid 300 is impractical for typical clinical settings. Accordingly, some known calibration methodologies simply use determined calibration values for a given position in grid 300 for other positions in grid 300. Alternatively, other known calibration methodologies permit amplitude ramping to occur more quickly by utilizing non-linear ramping steps based upon previously determined perception threshold and maximum tolerable values of nearby stimulation positions.

Some representative embodiments provide an efficient methodology to determine calibration values for a relatively large number of stimulation points while only requiring amplitude ramping and patient feedback for a relatively few number of stimulation positions. In some representative embodiments, calibration of stimulation points according to conventional methodologies occurs at points along the periphery of available stimulation points defined by the electrodes of one or several stimulation leads. Calibration values for other stimulation points are determined by employing selected linear interpolation techniques using the calibration values determined at the points along the periphery.

Figure 4:
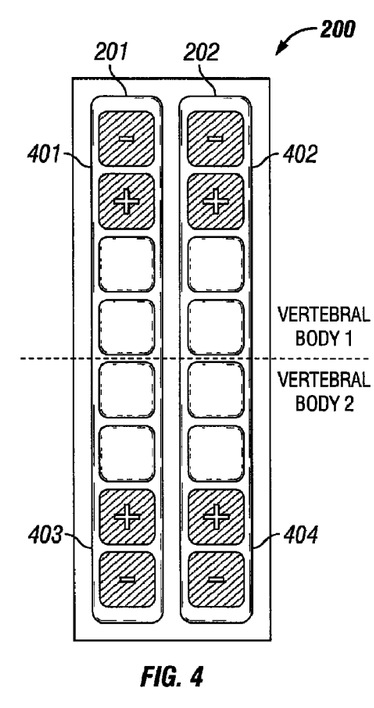
FIG. 4 depicts a lead arrangement including anode/cathode combinations that can be utilized for calibration purposes.

For example, FIG. 4 depicts lead arrangement 200 further including anode/cathode combinations 401-404 that can be utilized for calibration purposes according to one representative embodiment. In this example, anode/cathode combinations 401-404 are disposed at opposite ends and opposite sides of the electrode portions of the two stimulation leads 201, 202. Separate perception threshold and maximum tolerable amplitude values are determined for each of combinations 401-404 in response to patient feedback. Some representative embodiments then automatically calculate calibration values for other stimulation points.

Preferably, linear interpolation is performed for points along the boundary and a summation of boundary point interpolated values is performed for values within the boundary. Combinations 401-404 correspond to stimulation points (1, 1), (1, 8), (3, 1), and (3, 8) in grid 300. The boundary formed by these points are given by the segments (1, 1)-(1, 8), (3, 1)-(3, 8), (1, 1)-(3, 1), and (1, 8)-(3, 8). Stimulation points or positions interior to the boundary are given by points (2, 2) through (2, 7).

Figure 5:
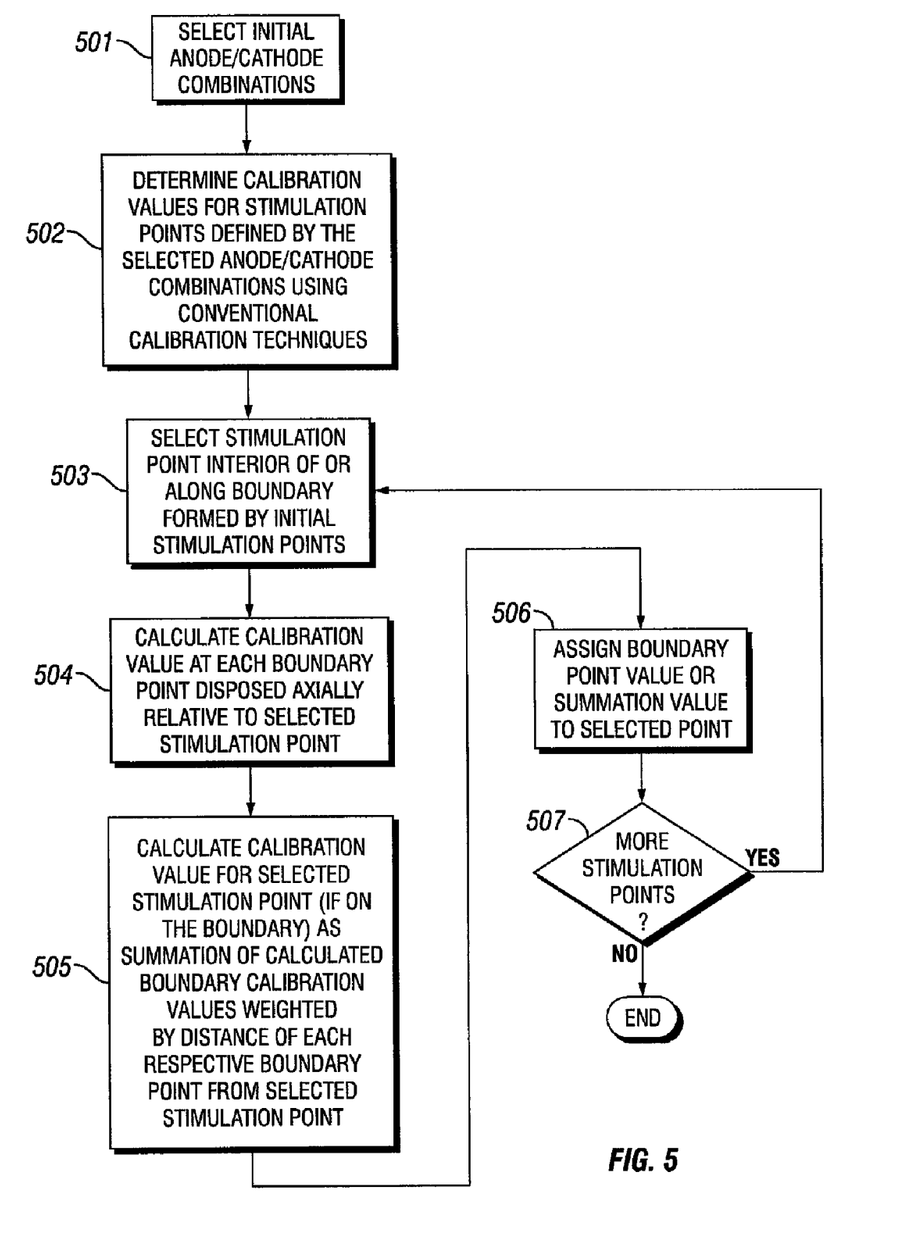
FIG. 5 depicts a flowchart for calculating calibration values using previously determined calibration parameters according to one representative embodiment.

FIG. 5 depicts a flowchart for determining calibration values according to some representative embodiments. In 501, initial anode/cathode combinations (e.g., combinations 401-404 as shown in FIG. 4) are selected. The initial anode/cathode combinations may be automatically selected by software on controller 110. Alternatively, the clinician may be given the ability to select the particular combinations for the initial calibration. Preferably, the anode/cathode combinations are at opposite peripheral portions of combinations possible for selection on the electrode lead(s). In 502, calibration values for stimulation points defined by the selected anode/cathode combinations are determined using conventional calibration techniques. For example, a respective perception threshold value may be determined by slowly ramping an amplitude of pulses applied to a patient for each combination until the patient indicates that the patient is able to perceive stimulation. A maximum tolerable value for each combination may be determined in a similar manner by ramping the amplitude of pulses applied to the patient until the patient indicates that the stimulation has become uncomfortable or painful.

Figure 6:
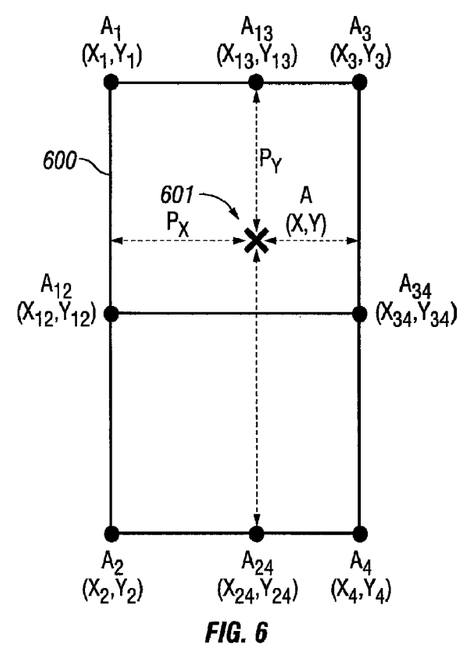
FIG. 6 depicts a boundary of stimulation points formed by initially calibrated stimulation points according to one representative embodiment.

A stimulation point interior to or along the boundary formed by initial stimulation points is selected (503). FIG. 6 depicts boundary 600 in which point 601 represents a selected point within the interior of boundary 600 formed by the initially calibrated stimulation points. The selection may occur using input from the clinician. Alternatively, the selection may be performed automatically by software in relation to the particular lead(s) implanted with a patient.

In the process flow of FIG. 5, a respective calibration value at each boundary point disposed axially (i.e., along the X-axis and the Y-axis) to the selected stimulation point is calculated (504). Referring to FIG. 6, coordinates (x, y) represent the location of the current selected stimulation point within boundary 600. Values $A_1$, $A_2$, $A_3$, and $A_4$, represent the determined calibration values at the initially calibrated stimulation points $(x_1, y_1)$, $(x_2, y_2)$, $(x_3, y_3)$, and $(x_4, y_4)$. For example, each of these values could represent a perception threshold value. The process flow of FIG. 5 could be repeated and these values could represent a maximum tolerable value. Points $(x_{12}, y_{12})$, $(x_{13}, y_{13})$, $(x_{24}, y_{24})$, and $(x_{34}, y_{34})$ are the points disposed axially relative to the selected stimulation point (x, y) on boundary 600. Values $A_{12}$, $A_{13}$, $A_{24}$, and $A_{34}$, represent the linearly interpolated calibration values at these points. For example, value $A_{12}$ is calculated by linearly interpolating between the values $A_1$ and $A_2$. These values are given by the following equations:

$$A_{12}=A_1+(A_1-A_2)*(y-y_1)/(y_1-y_2)$$

$$A_{13}=A_1+(A_1-A_3)*(x-x_1)/(x_1-x_3)$$

$$A_{24}=A_2+(A_2-A_4)*(x-x_2)/(x_2-x_4)$$

$$A_{34}=A_3+(A_3-A_4)*(y-y_3)/(y_3-y_4)$$

Referring again to FIG. 5, in 505, a calibration value for the selected stimulation point is then calculated as a summation of calculated boundary calibration values weighted by distance of respective boundary point from selected stimulation point (if the selected point is within the boundary). Referring to FIG. 6, the value $P_x$ represents the weighting factor used to weight values $A_{12}$ and $A_{34}$ and the value $P_y$ represents the weighting factor used to weight values $A_{13}$ and $A_{24}$. These weighting factors are determined by the relative distance of point (x, y) between two respective boundary points axially disposed on the boundary. $P_x$ is given by $(x-x_{12})/(x_{34}-x_{12})$ and $P_y$ is given by $(y-y_{24})/(y_{13}-y_{24})$. The summation to calculate the respective calibration value A for point (x, y) is then given by: $(\frac{1}{2})[A_{12}(1-P_x)+A_{34}(P_x)+A_{24}(1-P_y)+A_{13}(P_y)]$ One of the calculated values is assigned to the selected point (506). If the selected point is within the boundary, the calculated summation is assigned to the selected point for the respective calibration value. If the selected point is on the boundary, the respective boundary point interpolated value is utilized. For example, if the selected stimulation point is on the boundary along the segment between points $(x_1, y_1)$ and $(x_2, y_2)$, the value $A_{12}$ is assigned to the selected point. If more stimulation points require calculation of the calibration value(s) (507), the process flow is repeated by returning to 503 for selection of another stimulation point. If not, the process flow ends.

Figure 7A:
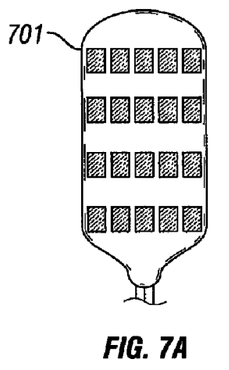
FIGS. 7A-7C depict example stimulation paddle-style leads including respective electrode arrangements.
Figure 7B:
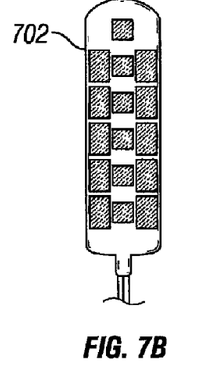
Figure 7C:
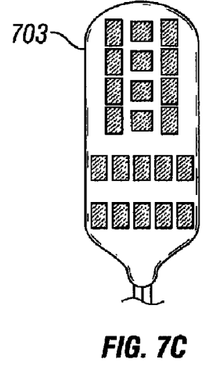
Figure 8:
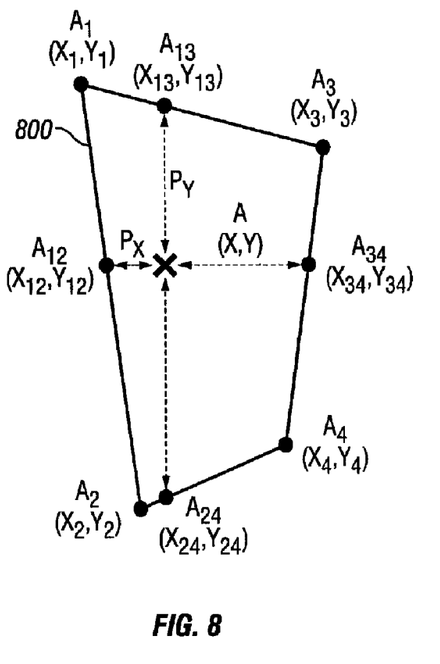
FIG. 8 depicts a stimulation boundary, formed by a selection of initially calibrated stimulation points, that does not have a rectangular form according to one representative embodiment.

Although FIG. 4 depicts electrodes arranged in a rectangular grid, other electrode arrangements may be utilized according to other embodiments. Calibration values can be calculated for the electrode arrangements on paddle leads 701-703 shown in FIGS. 7A-7C as examples. Data defining the electrode layouts of a variety of leads can be stored in memory of controller 110 for selection by the clinician. The selection of a particular layout can then be utilized to facilitate electrode selection for conventional calibration techniques and performance of subsequent calibration value calculations by the clinician. FIG. 8 depicts stimulation boundary 800, formed by a selection of initially calibrated stimulation points, that does not have a rectangular form. As previously discussed, the calculation of a respective calibration value A for point (x, y) occurs by linearly interpolating along the respective segments of boundary 800 for points $A_1$, $A_2$, $A_3$/and $A_4$ and calculating a summation of these values weighted by $P_x$ and $P_y$. Also, although the flowchart of FIG. 5 has described various calculations as separate steps, it is possible to reduce the separate calculations to a closed-form equation in a higher level programming language when implementing respective portions of the flowchart in software.

Figure 9:
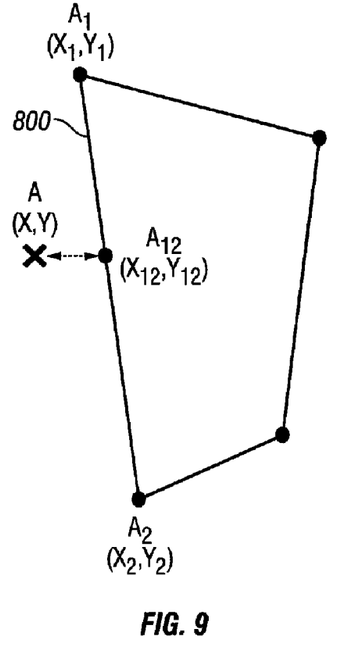
FIG. 9 depicts selection of a calibration value for a stimulation point lying outside of a boundary formed by initially calibrated stimulation points according to one representative embodiment.

Depending upon the electrode configuration of the lead(s) and the anode/cathode combinations initially selected for conventional calibration by the clinician, it is possible that certain stimulation points may be disposed outside of the boundary formed by the initial anode/cathode combinations. Referring to FIG. 9, when a point lies outside of the boundary, the calibration value for such a point is preferably set to equal the linearly interpolated calibration value of the closest boundary point having same longitudinal position along the Y-axis or lateral position along the X-axis as the case may be. In the case shown in FIG. 9, the value selected for point (x, y) would be the value $A_{12}$ at point $(x_{12}, y_{12})$ on boundary 800.

Although some embodiments calculate and determine calibration values at multiple points before additional programming operations occur, other embodiments may calculate calibration in a concurrent manner as programming operations occur. For example, a clinician may attempt to program stimulation parameters at various electrode locations. As the clinician performs such programming, some embodiments determine and store calibration parameters (e.g., comfort values) and when a suitable number of calibration parameters forming a suitable boundary (at least three points, but preferably four or more) are obtained, the calibration parameters within the boundary are preferably automatically calculated.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:
1. A method of using one or more calibration values for one or more stimulation leads implanted within the epidural space of a patient to control electrical stimulation of the patient, the method comprising:

selecting a plurality of electrodes of the one or more stimulation leads, the selected plurality of electrodes defining a two-dimensional region of stimulation points;

determining a respective calibration value for each stimulation point defined by the plurality of electrodes;

selecting a stimulation point within a boundary formed by the two-dimensional region;

identifying points on the boundary that are axially displaced relative to the selected stimulation point;

automatically calculating boundary calibration values for identified points on the boundary, each boundary calibration value being calculated as a linear interpolation of calibration values of a pair of stimulation points determined for the plurality of electrodes;

automatically assigning a calibration value to the selected stimulation point that is a weighted summation of the calculated boundary calibration values; and using the automatically assigned calibration value for the selected stimulation point to control an amplitude of stimulation pulses applied to the patient.

2. The method of claim 1 wherein the automatically assigned calibration value is a perception threshold value.

3. The method of claim 1 wherein the automatically assigned calibration value is a maximum tolerable value.

4. The method of claim 1 wherein the summation of the calculated boundary calibration values sums the calculated boundary calibration values using weighting factors that are related to distances between the selected stimulation point and the identified points on the boundary.

5. The method of claim 1 wherein the one or more stimulation leads comprise a plurality of percutaneous stimulation leads.

6. The method of claim 1 wherein the one or more stimulation leads comprise a paddle-style stimulation lead.

7. The method of claim 1 further comprising:
automatically assigning a calibration value to a stimulation point outside of the boundary that is equal to a linear interpolation of calibration values of a pair of stimulation points determined for the plurality of electrodes.

8. The method of claim 1 further comprising:
automatically assigning a calibration value to a stimulation point on the boundary that is equal to a linear interpolation of calibration values of a pair of stimulation points determined for the plurality of electrodes.

9. The method of claim 1 wherein the two-dimensional region has a rectangular form.

10. The method of claim 1 wherein the two-dimensional region has a non-rectangular form.

* * * * *